(12) United States Patent
Baust et al.

(10) Patent No.: US 10,196,598 B2
(45) Date of Patent: Feb. 5, 2019

(54) SYSTEM FOR HEATING AND COOLING SAMPLES

(71) Applicant: CPSI Holdings LLC, Owego, NY (US)

(72) Inventors: John M. Baust, Owego, NY (US); Joshua T. Smith, Owego, NY (US); William Corwin, Johnson City, NY (US); Kristi Snyder, Candor, NY (US); Anthony T. Robilotto, Binghamton, NY (US)

(73) Assignee: CPSI HOLDINGS LLC, Owego, NY (US)

(*) Notice: Subject to any disclaimer, the term of this patent is extended or adjusted under 35 U.S.C. 154(b) by 336 days.

(21) Appl. No.: 14/876,087

(22) Filed: Oct. 6, 2015

(65) Prior Publication Data

US 2016/0097583 A1 Apr. 7, 2016

Related U.S. Application Data

(60) Provisional application No. 62/060,891, filed on Oct. 7, 2014.

(51) Int. Cl.
| | |
|---|---|
| *C12M 1/34* | (2006.01) |
| *B01L 1/00* | (2006.01) |
| *B01L 7/00* | (2006.01) |
| *C12M 1/02* | (2006.01) |
| *C12M 1/36* | (2006.01) |

(52) U.S. Cl.
CPC .............. *C12M 41/12* (2013.01); *B01L 7/00* (2013.01); *C12M 41/22* (2013.01); *C12M 41/48* (2013.01); *B01L 2300/023* (2013.01); *B01L 2300/024* (2013.01); *B01L 2300/0809* (2013.01); *B01L 2300/0829* (2013.01); *B01L 2300/0854* (2013.01); *B01L 2300/0887* (2013.01); *B01L 2300/14* (2013.01); *B01L 2300/185* (2013.01); *B01L 2300/1822* (2013.01)

(58) Field of Classification Search
CPC ...... C12M 41/12; C12M 41/48; C12M 41/22; B01L 7/00; B01L 2300/0854; B01L 2300/0829; B01L 2300/1822; B01L 2300/024; B01L 2300/023; B01L 2300/185; B01L 2300/14; B01L 2300/0887; B01L 2300/0809
See application file for complete search history.

(56) References Cited

U.S. PATENT DOCUMENTS

| | | | | |
|---|---|---|---|---|
| 5,363,670 A | * | 11/1994 | Bartilucci | F25D 3/12 62/166 |
| 5,403,279 A | * | 4/1995 | Inaba | A61M 1/0245 600/584 |
| 5,603,220 A | * | 2/1997 | Seaman | A61J 1/165 62/3.62 |

(Continued)

*Primary Examiner* — Larry Furdge
(74) *Attorney, Agent, or Firm* — Hoffman Warnick LLC

(57) ABSTRACT

A system for heating or cooling a sample is disclosed, which includes an insulated chamber; at least one of a heater or a cooling pad disposed within the chamber; and at least one compliant, fluid filled pillow. The at least one compliant, fluid-filled pillow is disposed in the chamber and adjacent to the at least one thermal device while being heated or cooled to a desired temperature by the heater or the cooling pad, and upon reaching the desired temperature, the at least one compliant, fluid filled pillow substantially conforms to a container containing the sample.

20 Claims, 18 Drawing Sheets

(56) References Cited

U.S. PATENT DOCUMENTS

| | | | |
|---|---|---|---|
| 6,381,981 B1* | 5/2002 | Yaddgo | F25D 3/125 62/372 |
| 6,432,320 B1* | 8/2002 | Bonsignore | B82Y 30/00 165/10 |
| 6,596,531 B2 | 7/2003 | Campbell et al. | |
| 8,037,696 B2 | 10/2011 | Shaham et al. | |
| 2003/0082069 A1* | 5/2003 | Kuzyk | A01N 1/0284 422/1 |
| 2004/0265168 A1 | 12/2004 | Bakke | |
| 2007/0227719 A1 | 10/2007 | Voelker | |
| 2007/0231787 A1 | 10/2007 | Voelker | |
| 2010/0064698 A1* | 3/2010 | Schabron | F25D 3/08 62/62 |
| 2010/0281886 A1 | 11/2010 | Shaham et al. | |
| 2012/0122072 A1 | 5/2012 | Bilchinsky et al. | |
| 2013/0062038 A1 | 3/2013 | Pearson | |

* cited by examiner

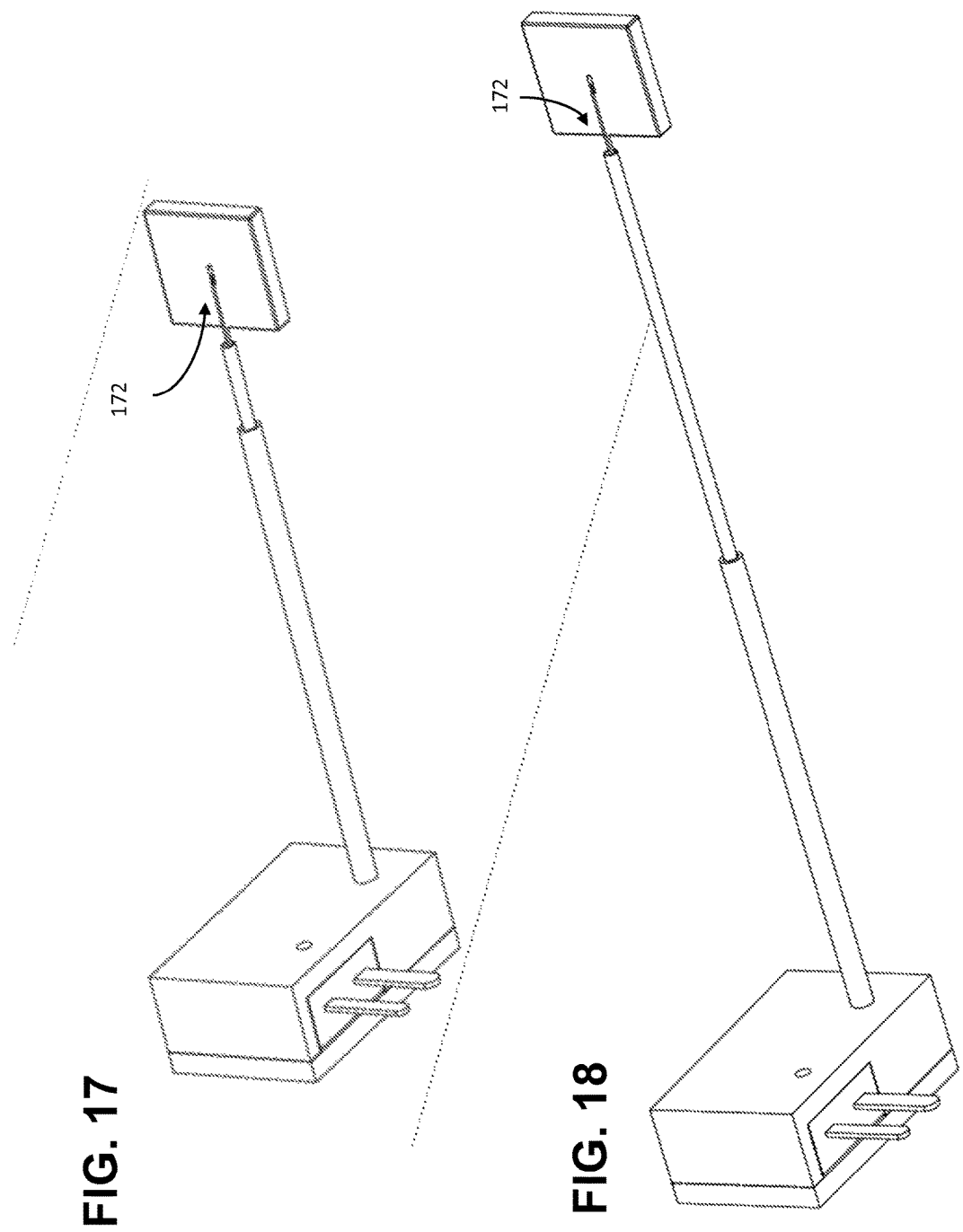

SYSTEM FOR HEATING AND COOLING SAMPLES

CROSS REFERENCE TO RELATED APPLICATIONS

This application claims the benefit of U.S. provisional application Ser. No. 62/060,891, filed Oct. 7, 2014, which is incorporated in its entirety as though fully set forth herein.

BACKGROUND OF THE INVENTION

Embodiments of the invention relate generally to a fluid-based heating and cooling system, and more particularly, to a system including compliant, fluid-filled sealed vessels for heating and cooling biological samples and other articles.

Cultured cells have emerged as a critical tool in biotechnology and biomedicine research and cell therapy. An unprecedented increase in the demand for cultured cell products is now driven by growth in biopharmaceuticals, cancer research, cell and gene therapy, and stem cell research. The integration of cells cultured in multi-well formats (typically 96- to 384-wells), cell function specific fluorescent probes, laser scanning fluorescent (plus UV and visible light) plate readers, and supporting robotics has created a powerful tool in cultured cell products in support of research in biopharmaceuticals (drug discovery), vaccine development, stem cell research, cell and gene therapy, toxicological testing, cosmetics, bio-defense, diagnostic healthcare, environmental monitoring, and basic sciences research.

In order to facilitate production, on-hand inventory for on-demand use, and subsequent distribution of cell- and tissue-based products for therapeutic, research, and consumer-based use, product freezing (cryopreservation) has emerged as a necessary and critical part of the process. To this end, numerous protocols, devices, solutions, and thousands of studies have been published on better ways to freeze biologics.

As with freezing, the thawing process has a critical impact on product quality and downstream utility. Warm (37° C.) water baths have been used in the cell therapy and research communities to thaw samples in various container formats, including vials, straws, bags, syringes, ampules, dishes and culture plates. Although warm water baths provide rapid and effective thawing of samples, there are a number of challenges associated with the process including but not limited to sterility, consistency, controllability, documentation and cleanliness. Dry thawing systems have also been used, but only in limited applications such as, e.g., blood banking, and thawing of blood component and plasma products frozen in bags to the exclusion of other container formats. Such systems are limited in compatible container formats, the thermal profiles that can be generated, and other parameters.

In the consumer market, a similar void exists for a warming device for a variety of applications, including but not limited to rapid thawing of frozen food, or as a therapeutic device to soothe and treat muscular and soft tissue injuries.

Accordingly, there is a need for a device and method to allow for controlled, multi-sample, high volume, reproducible, rapid warming or thawing of samples including, e.g., cells, tissues, DNA, proteins and antibodies, vaccines, and viruses, that are compatible with research, clinical, and consumer settings.

BRIEF DESCRIPTION OF THE INVENTION

One aspect of the disclosure provides a system for controlling the temperature of a sample, the system comprising: an insulated chamber; at least one of a thermal device (e.g., a heating pad or device or a cooling pad or device) disposed within the chamber; and at least one compliant, fluid filled pillow. The at least one compliant, fluid-filled pillow is disposed within the chamber and in physical contact with the at least one thermal device while the thermal device is heated or cooled to a pre-defined (e.g., preset or user-defined) temperature. The fluid-filled pillow is also in physical contact with, and substantially conforms to, the outer surface of a container containing a sample. Upon reaching the desired temperature, at least one compliant, fluid filled pillow substantially conforms to a container containing the sample when the sample is placed into the system.

A second aspect of the disclosure provides a method of heating or cooling a sample. The method includes placing the biological sample in physical contact with at least one compliant, fluid-filled pillow, wherein the physical contact includes contact between a majority of a surface area of the biological sample and the at least one compliant, fluid-filled pillow. The fluid-filled pillow may be heated or cooled by one or more thermal device also in physical contact with the fluid-filled pillow.

These and other aspects, advantages and salient features of the invention will become apparent from the following detailed description, which, when taken in conjunction with the annexed drawings, where like parts are designated by like reference characters throughout the drawings, disclose embodiments of the invention.

BRIEF DESCRIPTION OF THE DRAWINGS

FIGS. 17 and 18 show perspective views of a temperature measurement device assembly according to an embodiment of the invention.

Figure 1:
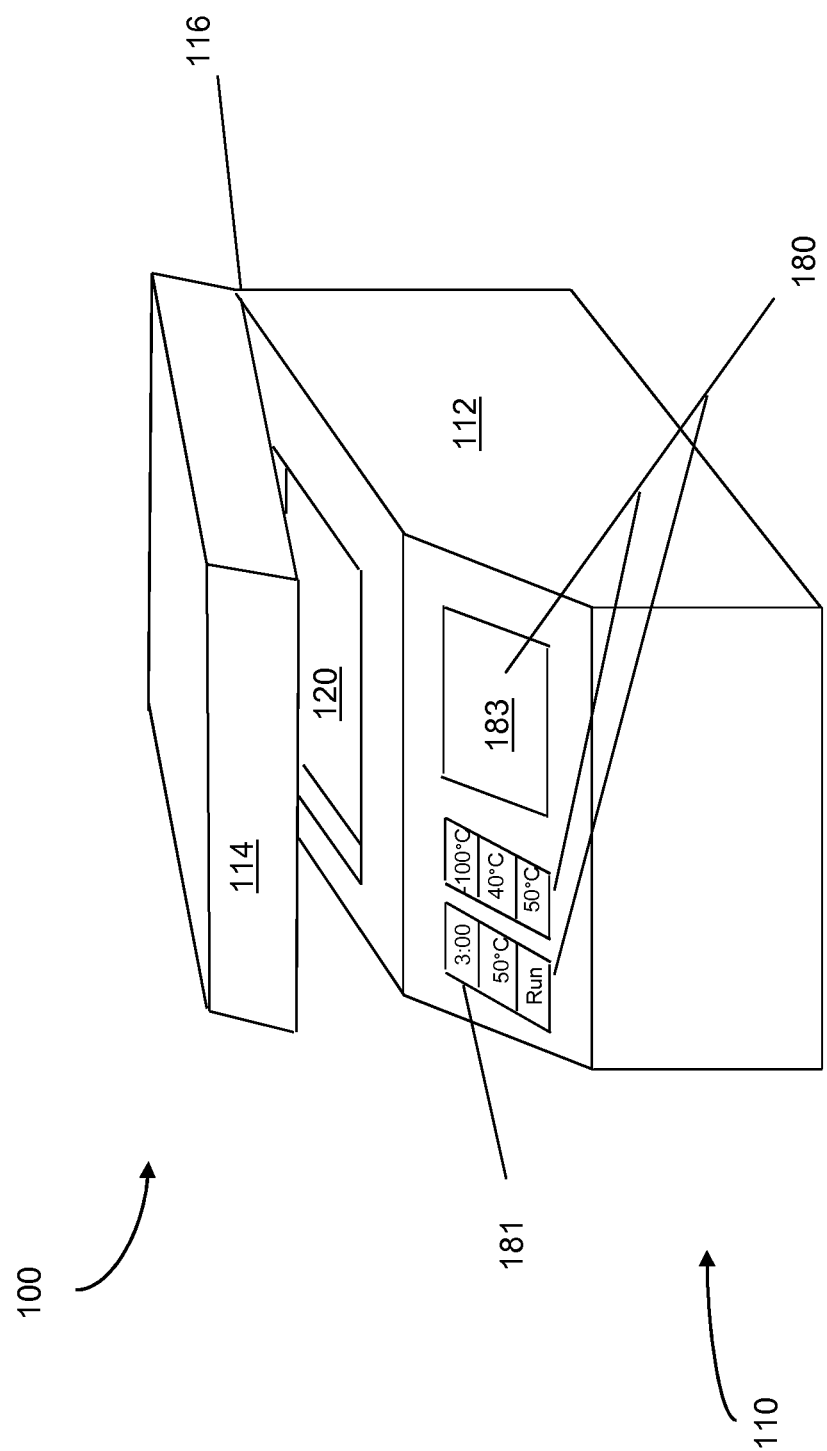
FIG. 1 shows a perspective view of a console unit that is part of a heating and cooling system, according to an embodiment of the invention.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION OF THE INVENTION

At least one embodiment of the present invention is described below in reference to its application in connection with the operation of a heating system. Although embodiments of the invention are illustrated in FIGS. 1-19 relative to a fluid-filled pillow- or sac-based heating system, it is understood that the teachings are equally applicable to devices, systems, and methods for controlling temperature of a sample or other article in other ways, such as cooling. Further, at least one embodiment of the present invention is described below in reference to a nominal size and including a set of nominal dimensions. However, it should be apparent to those skilled in the art that the present invention is likewise applicable to any suitable system. Further, it should be apparent to those skilled in the art that the present invention is likewise applicable to various scales of the nominal size and/or nominal dimensions.

As discussed above, FIGS. 1-19 illustrate various aspects of a heating and cooling system 100. With reference to FIG. 1, system 100 may include a console unit 110 having an integrated temperature controlled chamber 120. Console unit 110 has a shape and set of exterior dimensions selected such that console unit 110 may be portable and readily usable at a lab bench top. For example, one console unit 110 embodiment may have outer dimensions of approximately 35.6 cm (14 inches) wide×35.6 cm (14 inches) deep×30.5 cm (12 inches) high, and an approximate weight less than 4.5 kg. (10 lbs.). These dimensions are only one example; console units having larger or smaller dimensions and/or varied proportions and weights may be used for various types, quantities, and sizes of samples. Console unit 110 may include a base 112 and lid 114, which in some embodiments may be coupled to the base 112 by a hinge 116. Console unit 110 may also include a carrying handle 118 (FIGS. 15-16).

Figure 2:
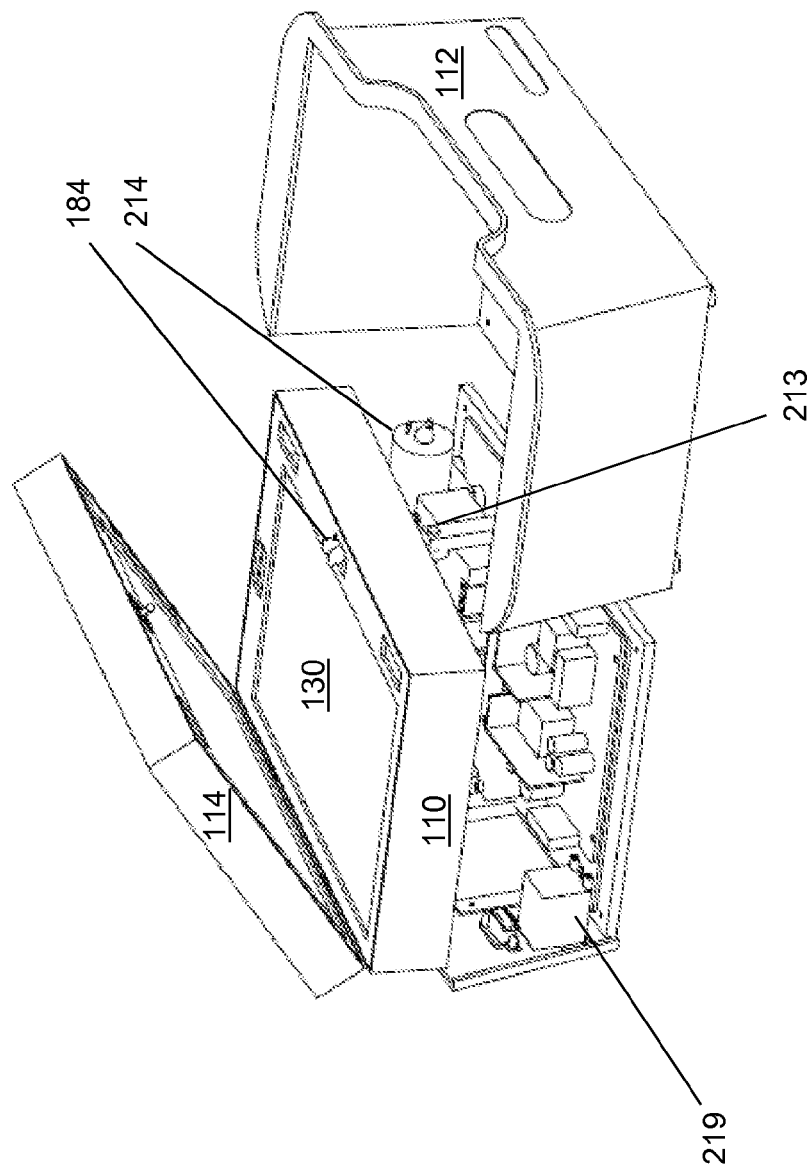
FIG. 2 shows an exploded perspective view of a console unit that is part of a heating and cooling system according to an embodiment of the invention.
Figure 3:
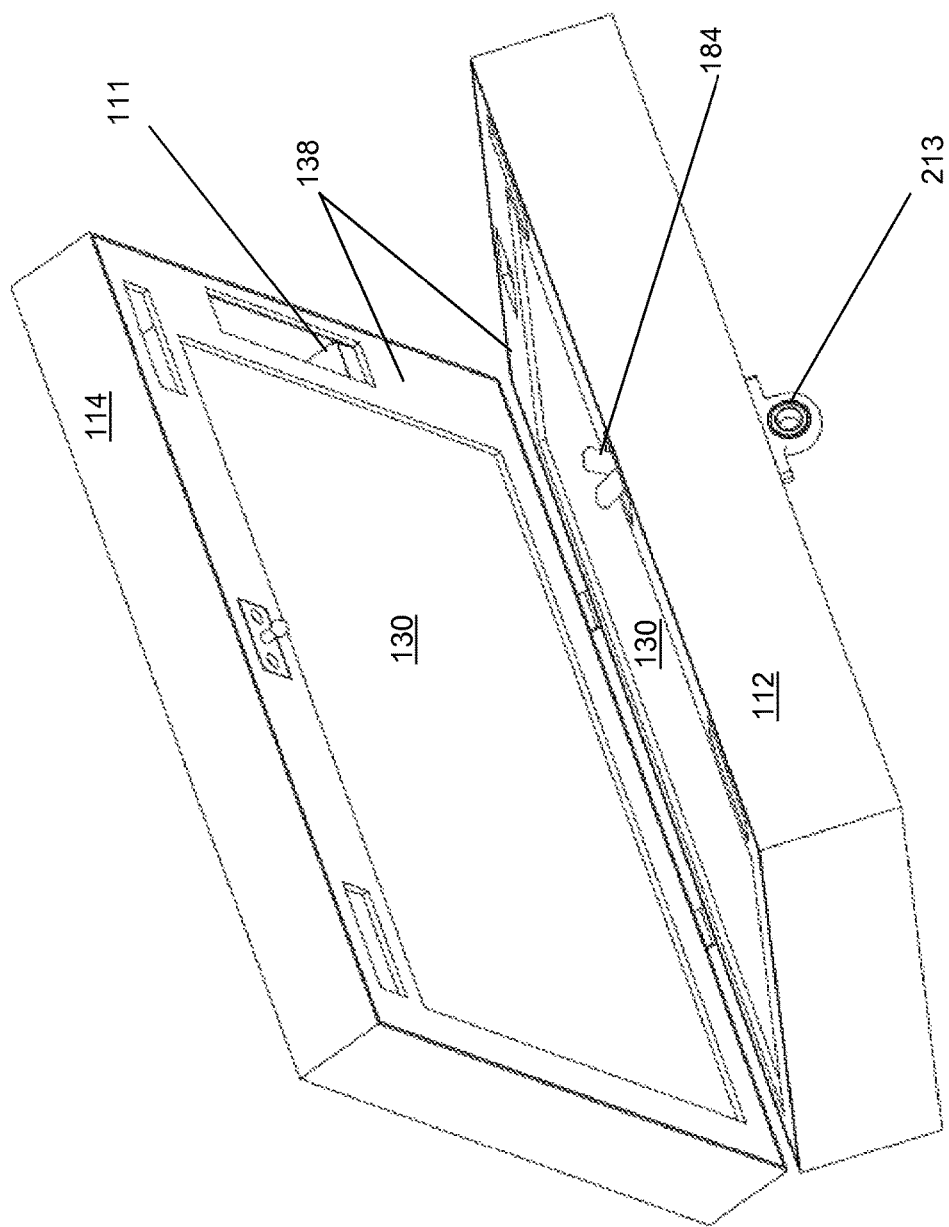
FIG. 3 shows a perspective view of a portion of a console unit that is part of a heating and cooling system according to an embodiment of the invention.
Figure 4:
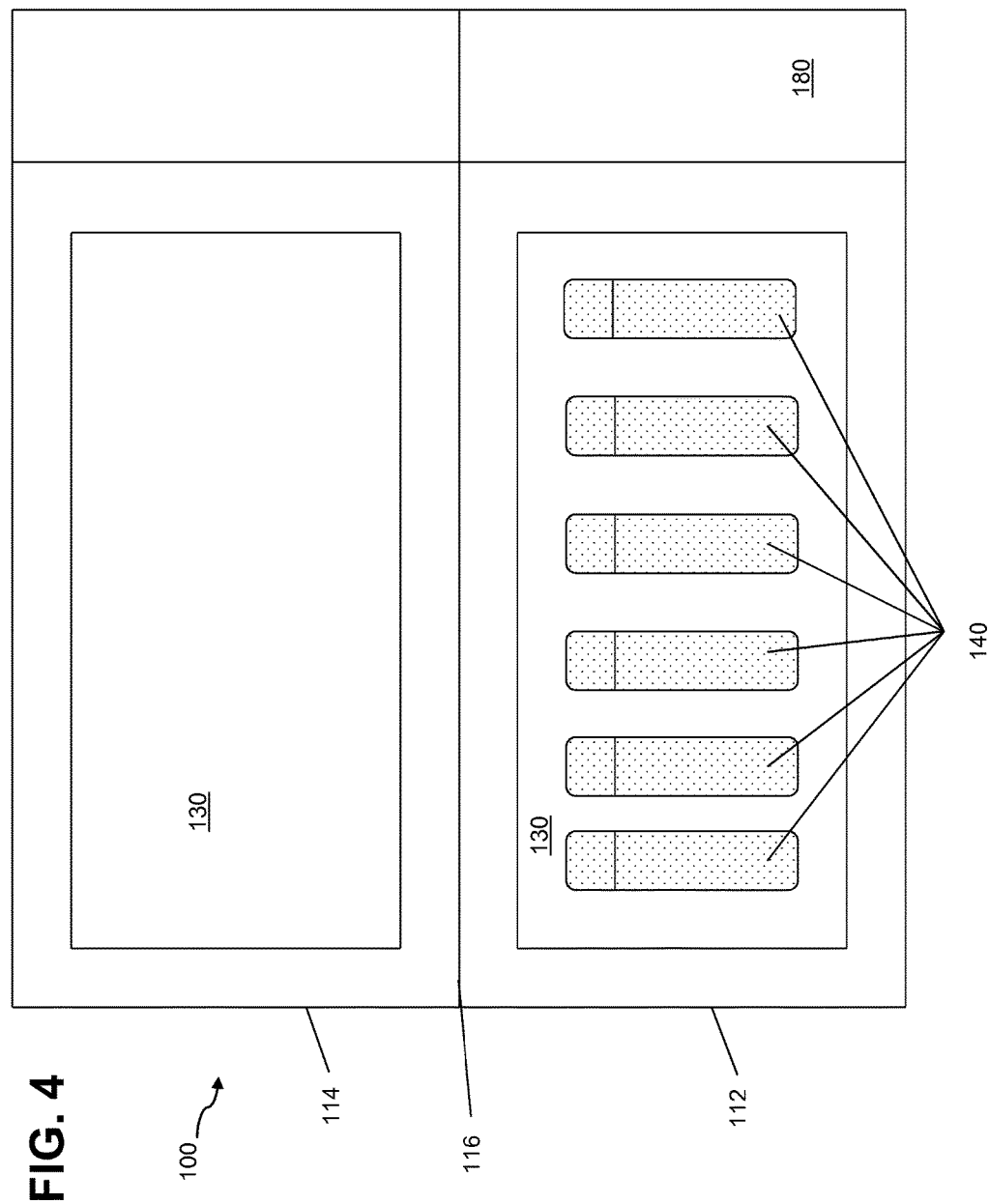
FIG. 4 shows a top view of a console unit similar to that of FIG. 1 with the lid open, according to an embodiment of the invention.

FIGS. 2-4 illustrate additional features of console unit 110. Temperature control chamber 120 within console unit 110 may include one or more pliable, flexible, compliant or semi-compliant, fluid-filled pillows 130 disposed therein. Pillows 130 can also be described as bag-like sacs, bladders, or vessels made of any of a variety of materials, e.g., flexible plastics, metallic materials, metallized plastics, metal (e.g., aluminum) foils, other metals such as gold, silver, or copper, thermoplastics, and/or waterproof fabrics or leather. In further embodiments (FIG. 8), pillows 130 may comprise a pillow frame 132 that defines the height and perimeter of the pillow 130, and a first, lower sheet or film 134 and a second, upper sheet or film 136 that define a bottom and top surface, respectively of pillow 130. A pillow retaining mask 138 may be provided to matingly engage with an upper peripheral surface of console base 112, and to retain pillow frame 132 within base 112. Retaining mask 138 may overlap with the perimeter of pillows 130, but may include an opening that exposes a substantial portion to a majority of the upper surface of second, top pillow sheet 136. The second pillow 130, which may be disposed in console lid 114, may be retained within lid 114 in a substantially similar manner (albeit of opposite upper and lower orientation).

Pillows 130 are sealed or sealable and contain a fluid having a relatively high specific heat capacity (e.g. typically greater than 1 kJ/kg K and more often between 1 kJ/kg K and 5 kJ/kg K), and may be used for warming or for cooling. Example fluids may include liquids, foams, or gels, and may more particularly include water, alcohols, oils or petroleum products, ethylene glycol, aqueous solutions, suspensions, or slurries, or slurries/solutions including suspended solid filings or shot-like materials or particles of, e.g., metals such as steel, copper, aluminum, gold, silver, titanium, etc., sapphire, diamond, or quartz, or any other material known to increase heat transfer, capacity, stability, or retention within pillow 130. In some embodiments, pillows 130 may be made of plastic and may be filled with water.

Figure 8:
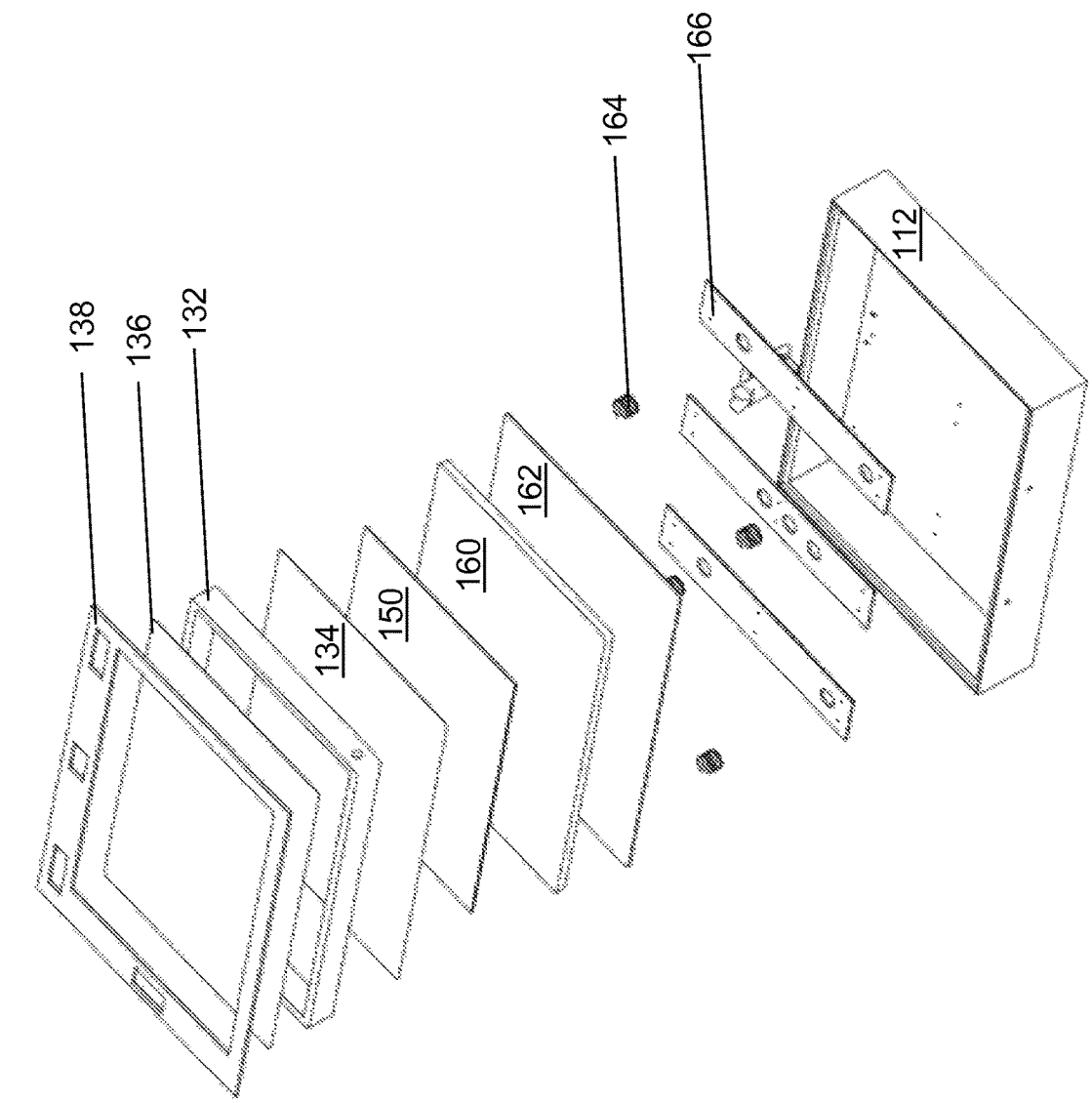
FIG. 8 shows an exploded perspective view of a portion of a console unit that is part of a heating and cooling system according to an embodiment of the invention.

Pillows 130 may be arranged in temperature control chamber 120 in a number of ways. In the embodiment shown in, e.g., FIGS. 2-3, a first pillow 130 may be disposed within the temperature control chamber 120 in console base 112, and a second pillow 130 may be disposed in the console lid 114. FIGS. 3 and 8 illustrate one embodiment according to which the first pillow 130 is installed in console base 112.

When a sample 140 is placed on or against the first pillow 130, the compliant surface of each pillow 130 substantially conforms to the shape of the container holding sample 140. By substantial conformance, it is meant that the surface of pillow 130 forms or deforms such that it is in physical contact with a large proportion of an outer surface of the container holding sample 140. In some embodiments, the large proportion may be a majority of the surface area of the sample container, or substantially all of the surface area of the sample container. The flexibility and compliance of the outer surface of pillows 130 provides compatibility with a variety of sample container formats including but not limited to vials, straws, bags, syringes, ampules, dishes and culture plates. In applications in which pillows 130 are used for heating or cooling respectively, the fluid contained within pillows 130 is heated or cooled to a desired temperature, as will be discussed in greater detail below.

As shown in, e.g., FIGS. 4-7, a sample 140 may be placed against the one or more pillows 130 within chamber 120. In particular, two or more pillows may be used in a configuration similar to that of FIGS. 2-3, and the sample 140 may be placed on first pillow 130. When console lid 114 including the second pillow 130 is closed, the samples or samples 140 are sandwiched between two pillows 130 to collectively provide contact with substantially the entire sample container surface. In FIG. 4, a first pillow 130 is disposed within console base 112, and a plurality of containers of samples 140 are placed on the first pillow 130 in base 112. A second pillow 130 is disposed within or attached to lid 114, such that when lid 114 is closed, as in FIGS. 5-7, samples 140 are in physical contact with, and substantially surrounded by, the two pillows 130. The compliance of the outer surface of each pillow 130 facilitates efficient heat exchange between the pillows 130 and the fluid contained therein, and the sample 140 to be heated or cooled.

It is noted that pillows 130 need not be disposed specifically in the unit base 112 and lid 114 as shown in FIGS. 2-7; various arrangements are possible as will be appreciated by one of skill in the art. In some embodiments, pillows 130 may be movable/adjustable in position. In further embodiments, other numbers, shapes, and configurations/arrangements of pillows 130 may be used. For example, any number of pillows 130 ranging from, e.g., one to ten pillows or more can be incorporated in an individual or multiple sandwich configuration depending on the application. In another embodiment (see, e.g., FIG. 16), multiple single pillows 130 may be used, allowing for sequential individual use of pillows. In still further instances, multiple sandwich pillows may be used for thawing multiple samples, where independent control of each sample is desired. In further embodiments, samples may be placed individually onto pillows 130 or contained within a rack or fixture type of apparatus to allow for more convenient sample handling.

Figure 5:
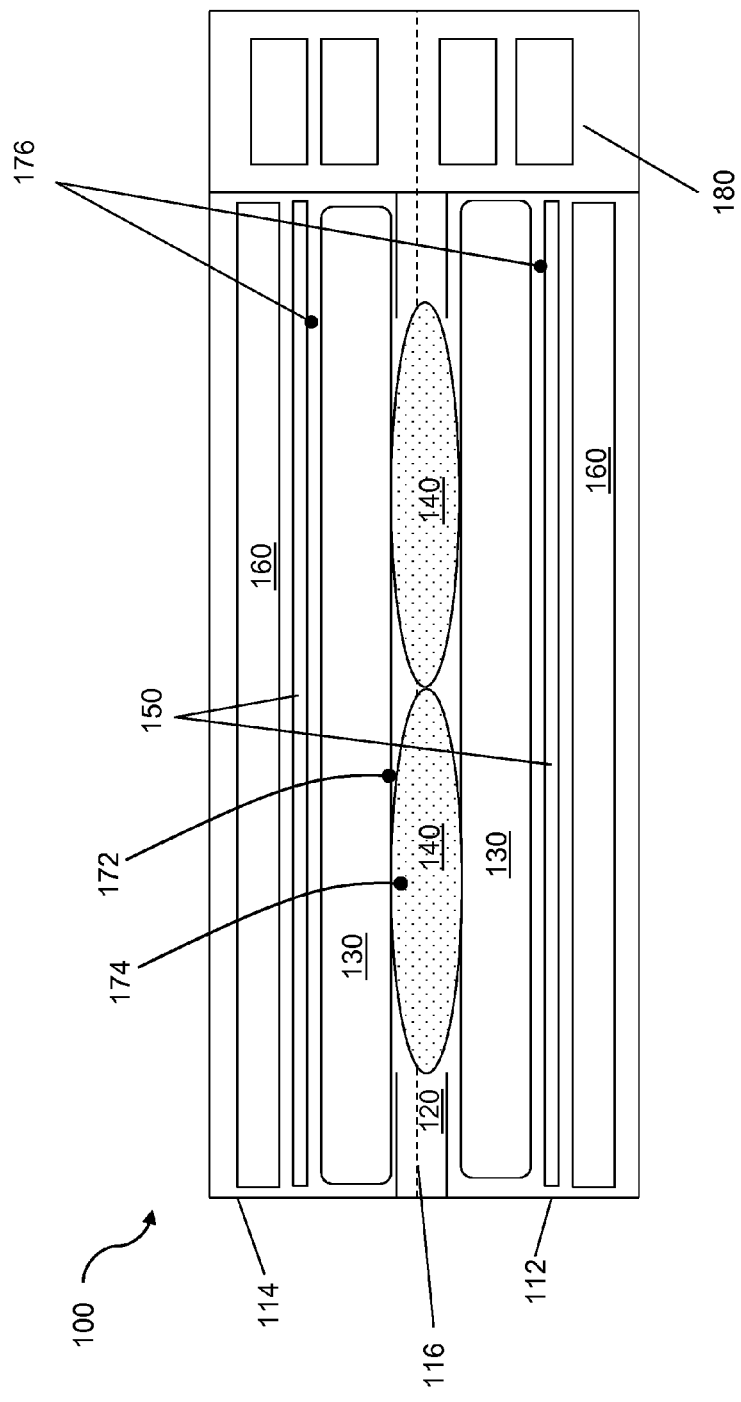
FIG. 5 shows a cross sectional view of a console unit similar to that of FIG. 1 with the lid closed, according to an embodiment of the invention.
Figure 6:
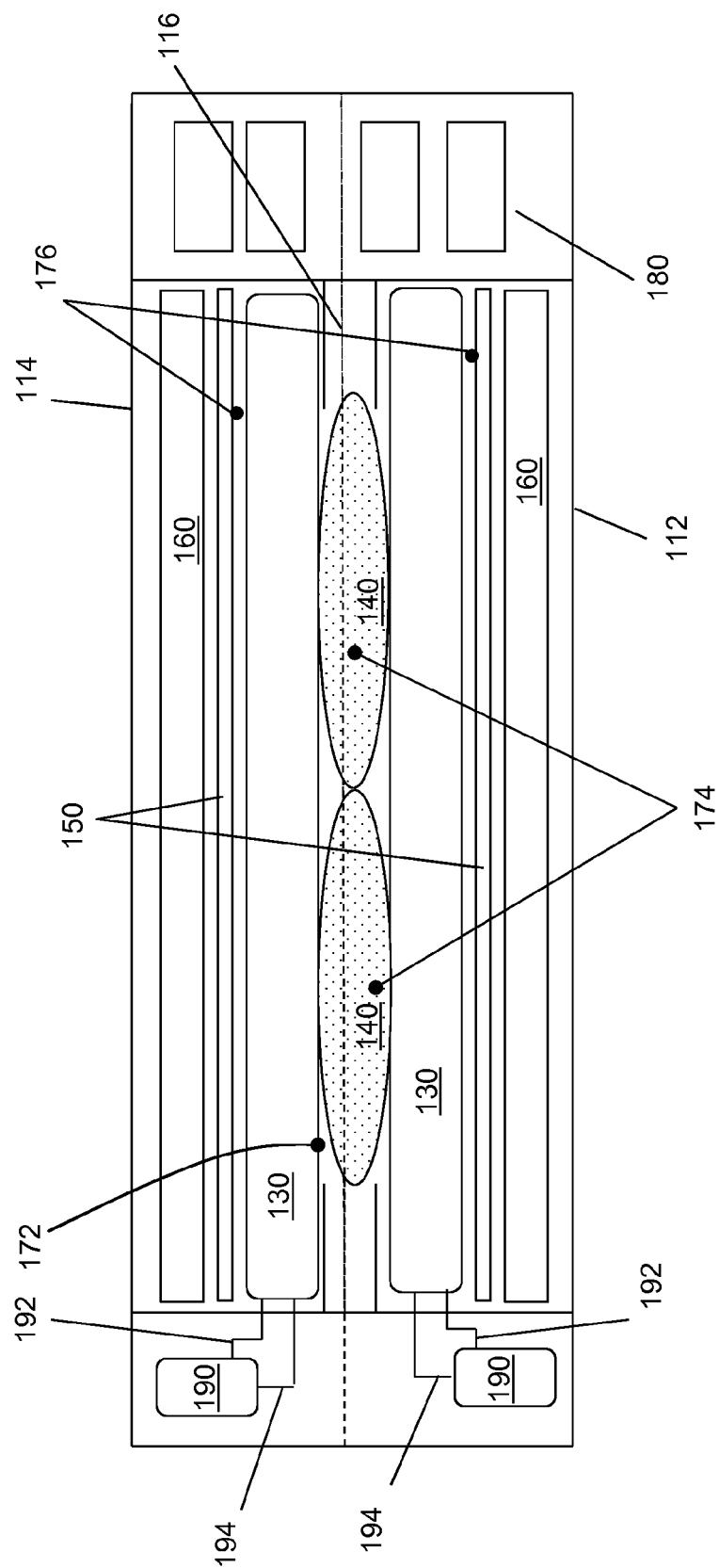
FIG. 6 shows a cross sectional view of a console unit including an integrated circulating pump, according to an embodiment of the invention.
Figure 7:
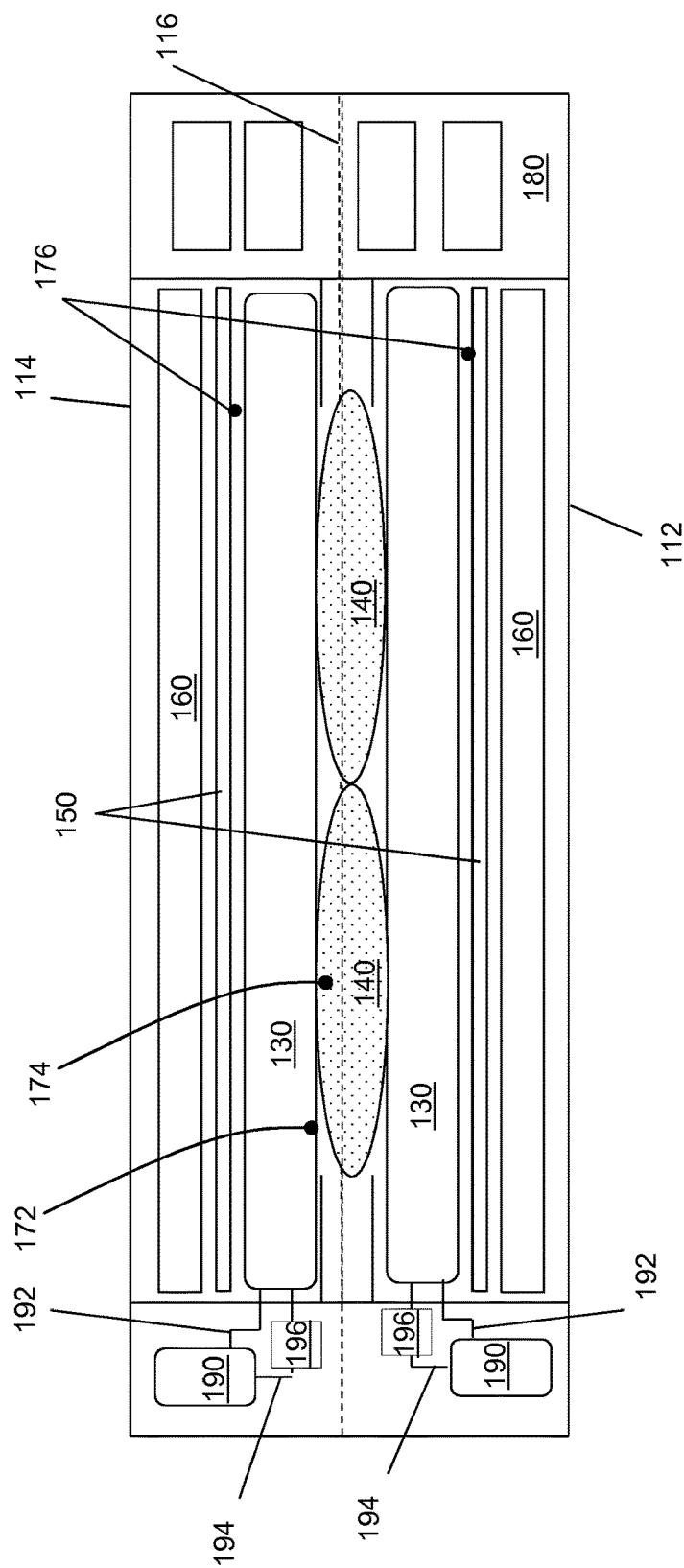
FIG. 7 shows a cross sectional view of a console unit including an integrated circulating pump and a cooling unit, according to an embodiment of the invention.

With reference to FIGS. 5-7, thermal devices 150 are provided for warming the fluid in the pillows 130, and therefore the internal temperature of chamber 120. Thermal devices 150 may either be heating devices, e.g., thermoelectric heating pads or Peltier, cartridge, resistance wire or heat pump heaters, or cooling devices, e.g., a Peltier device, refrigeration pump, or other cooling device, on/against which pillows 130 may be placed. The thermal devices 150, and thus the temperature of pillows 130 and the internal temperature of chamber 120, can be set to any preset or user-specified temperature within a range of temperatures over which the console unit 110 is effective. For example, the console unit 110 may warm samples 140 to any temperature between room temperature (nominally 18° C.) and approximately 90° C., or between about 30° C. and about 70° C., or may cool samples to any temperature below room temperature and about −40° C. or greater, or between about 10° C. and about −20° C.

Once the desired temperature is set, the unit heats up or cools down to the desired temperature by activating thermal device 150, which may be disposed beneath or alongside pillow 130. Temperature control chamber 120 may be thermally insulated by insulation 160 to assist in maintaining the desired temperature. Insulation 160 may be, e.g., foam-based insulation, spray foam, fiberglass, or other thermally insulating material as will be appreciated by one skilled in the art. The desired temperature of thermal devices 150 may be set by a user via a control panel or other user input device 181, which may be integrated with console unit 110, e.g., disposed on an exterior thereof, or may be part of an external computing device 182 that may be part of system control center 180. System control center 180 is discussed in greater detail below.

Figure 13:
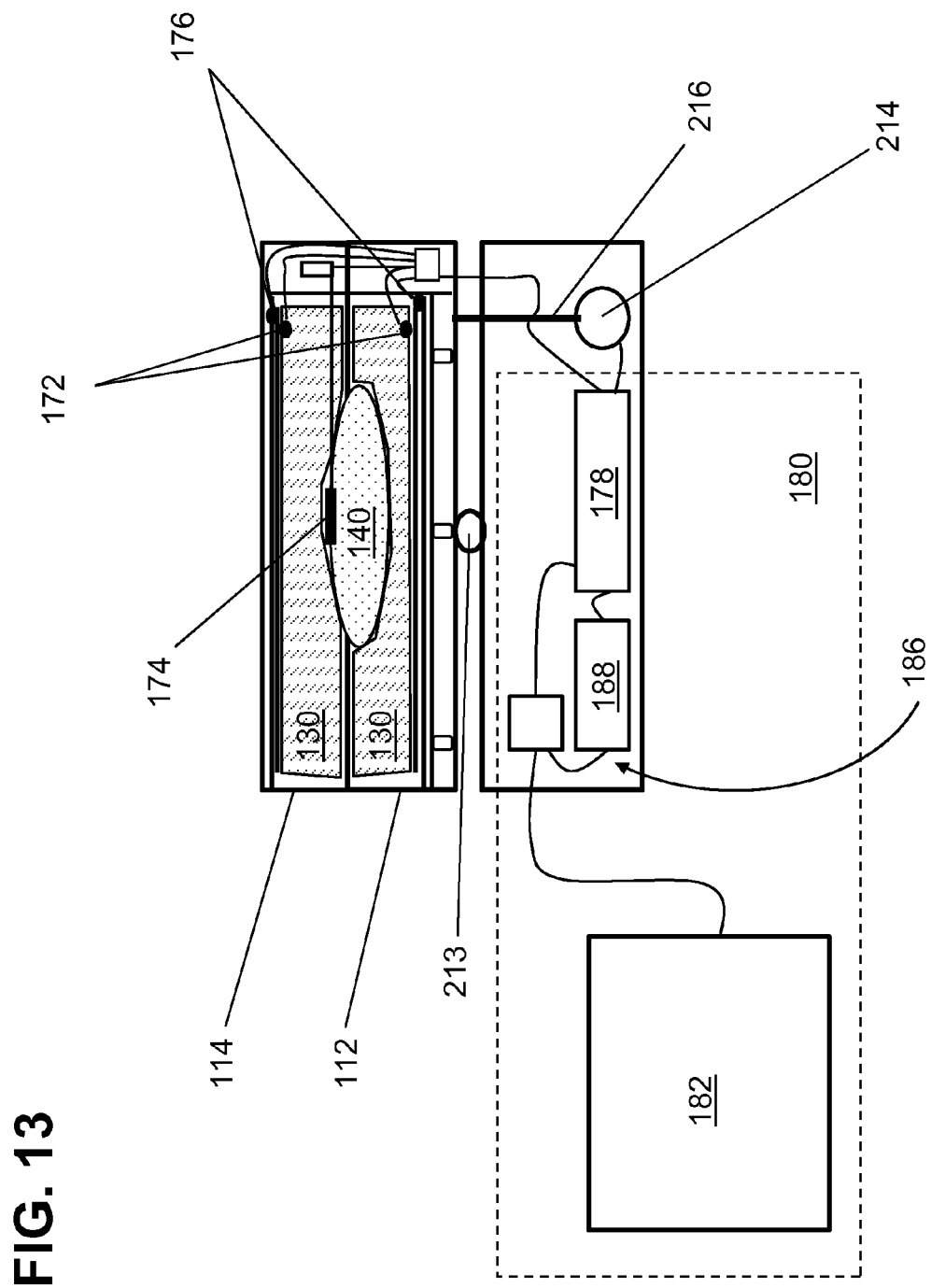
FIG. 13 shows a cross schematic view of aspects of the system control center in an embodiment of the invention.

Console base 112 may further include a pressure adjusting baseplate 162. Adjustable baseplate 162 may provide for application of a substantially constant pressure of the pillows 130 on sample 140 (FIGS. 8 and 13). In particular, it provides pressure in a relatively upward direction from beneath first pillow 130, pressing the first pillow 130 against the second pillow 130, where the second pillow 130 is located above the first pillow 130 (e.g., in console lid 114). This allows for different sizes, volumes, and shapes of sample containers to be placed into the system while maintaining adequate pressure to sandwich the sample between the pillows 130 during the heating/cooling. The adjustable baseplate 162 may be mounted on springs 164, which may be affixed on one end to baseplate 162, and on another end to baseplate spring holding frames 166, which may in turn be affixed to the lower portion of console base 112.

Figure 9:
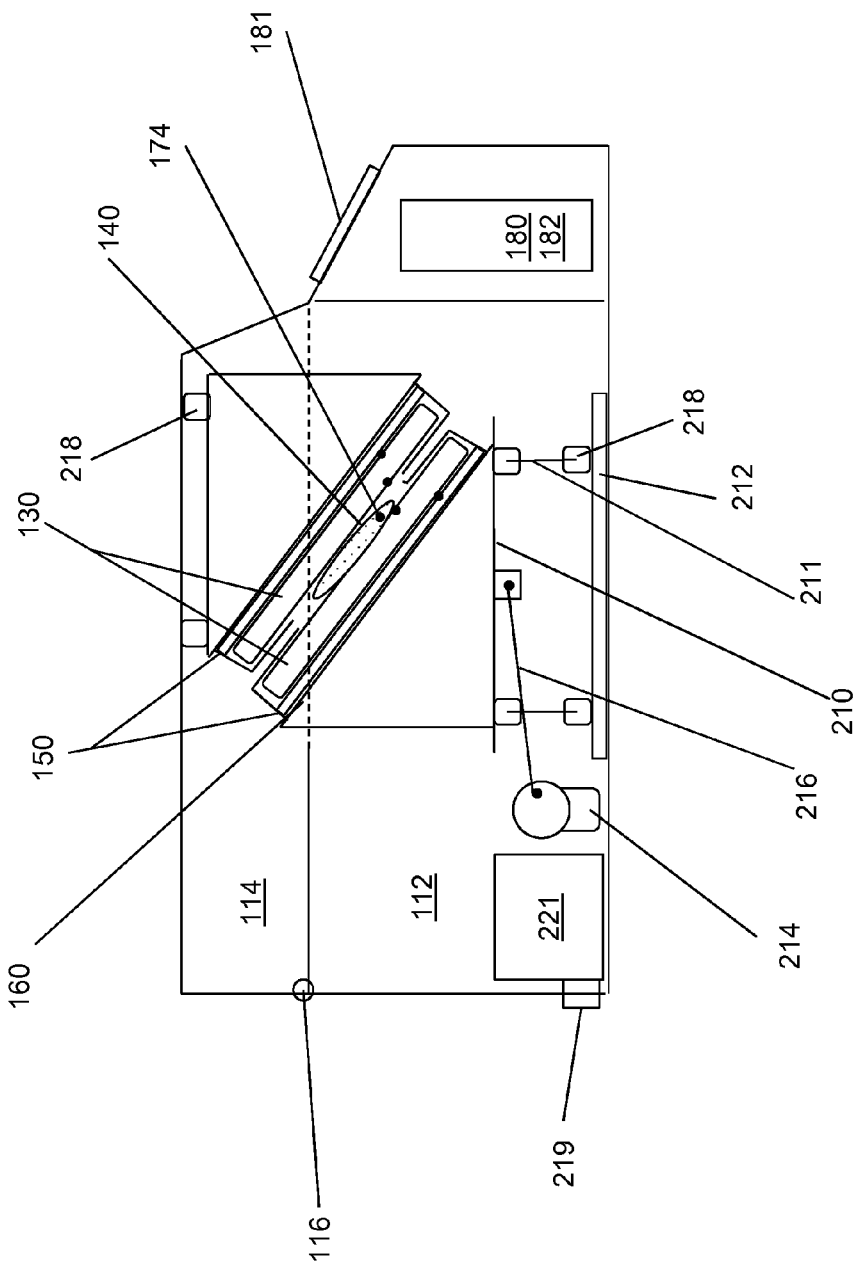
FIG. 9 shows a cross sectional view of a console unit including an inclined sample motion table, according to an embodiment of the invention.
Figure 10:
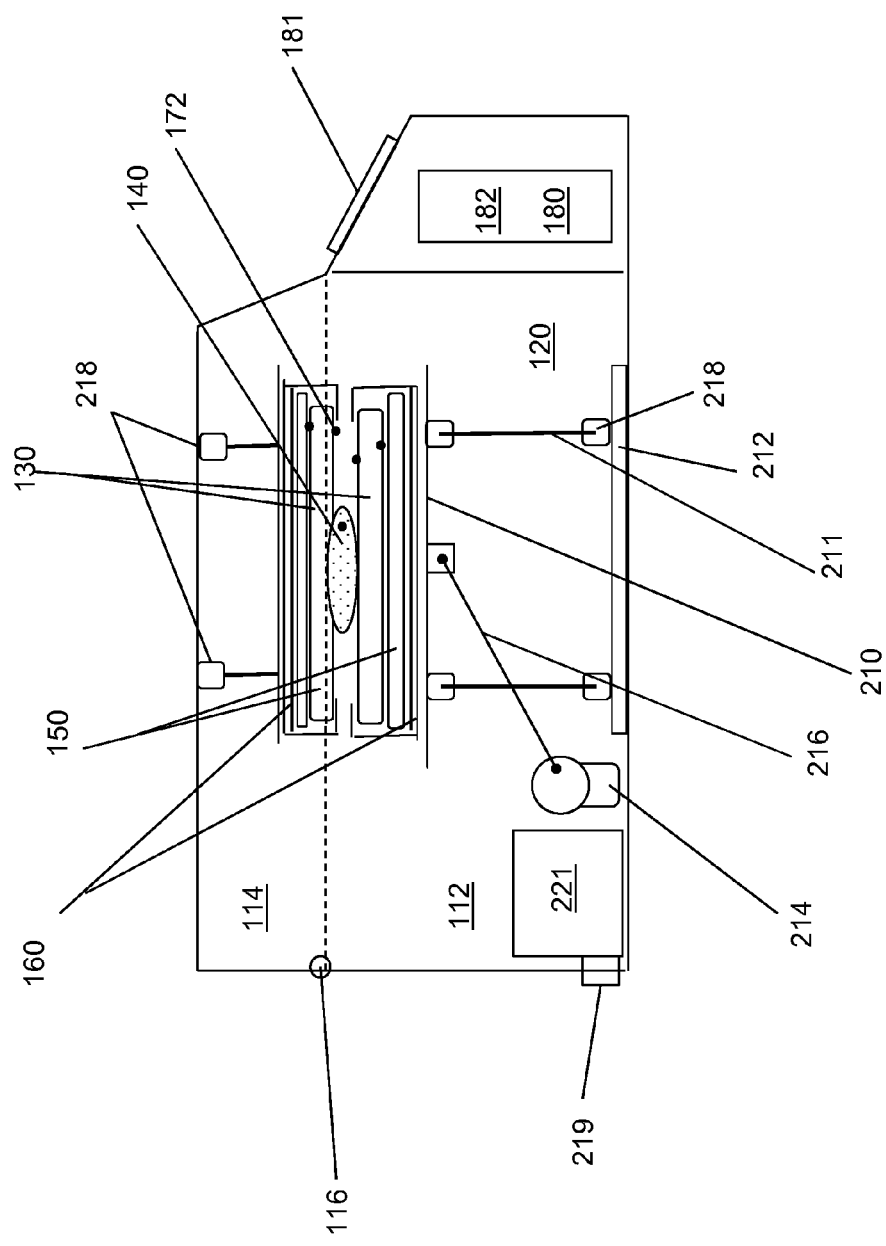
FIGS. 10 and 11 show cross sectional views of console units each including a horizontal sample motion table, according to embodiments of the invention.
Figure 11:
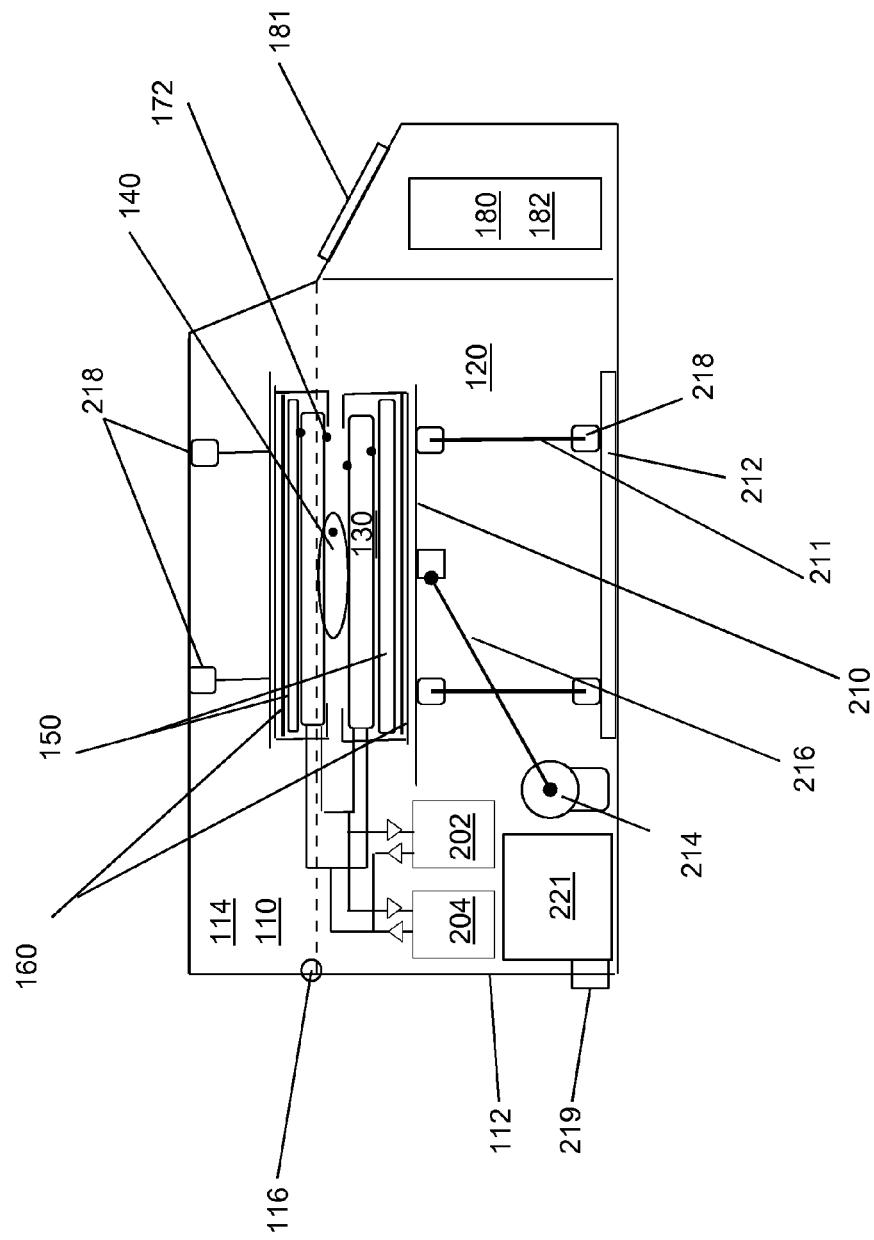

Turning next to FIGS. 9-11, console unit 110 may further include a motion table 210 for mixing a sample that is in the process of being heated (or cooled). Mixing sample(s) 140 during the heating/cooling process reduces the thermal gradient within both pillows 130 and samples 140, and increases thermal uniformity. Motion table 210 may be positioned within chamber 120, beneath pillows 130, thermal devices 150, and insulation 160, and may provide movements such as oscillation (FIGS. 9-11), rocking (FIG. 13), vibration, and rotation of samples 140 and pillows 130 to facilitate more uniform and efficient sample warming. As shown in FIGS. 9-11, motion table 210 may be supported within chamber 120 by motion standoffs or vertical supports 211, which support motion table 210 above an anchor platform 212. Movement of motion table 210 may be generated by a motor and flywheel 214 (FIG. 12), the movement of which is translated to movement of a motion drive shaft 216, which is coupled to motion table 210. In other embodiments, as shown in FIG. 13, rocking movement of motion table 210 is generated on rocker bearing 213, which acts as a center pivot point. It is noted, however, that rocker bearing 213 need not be located directly in the center of motion table 210; it may alternative be offset from center.

Console unit 110 may further include vibration dampeners 218 to reduce vibration associated with motion table 210. In various embodiments, motion table 210 may be angled or inclined as in FIG. 9, substantially horizontal as in FIGS. 10-11, may rock between angled and horizontal positions as in FIG. 13, may be substantially vertical, or have any other orientation as desired for a particular configuration. For example, samples 140 contained in vials or ampules may be thawed using an incline or vertical configuration; a cell therapy bag, IV bag, or plasma bag may be thawed using a horizontal or vertical configuration; and for food thawing, a vertical or horizontal configuration may be desired.

The fluid contained in pillows 130 is typically contained in a closed loop system, but may or may not be contained entirely within static sealed pillows 130 as shown in, e.g., FIG. 5. In the embodiment shown in FIG. 6, each pillow 130 may be fluidly connected with (or contain) a circulating pump 190 via a flow line in 192 and a flow line out 194. Circulating pump 190 may circulate the fluid within each pillow 130 during pre-warming and/or sample heating/cooling to promote thorough and even heating/cooling. The circulation loops including pillow 130 and circulating pump 190 may further contain an in-line heater and/or in-line cooling unit 196 (FIG. 7) to further increase system responsiveness to temperature change due to heat extraction by sample 140, i.e., pillow 130 fluid cooling during a heating process, to aid in a cooling process, or in heating processes to avoid or mitigate damage due to over-warming of sample 140. Cooling unit 196 may be an in-line part of the closed loop in which fluid circulates between a circulating pump 190 and a pillow 130. Cooling unit 196 may be activated to reduce pillow 130 temperature to a desired temperature to reduce potential overheating damage to sample 140 and to increase sample usage/hold window post thaw.

In various embodiments, circulating pump 190 may be integrated within device 110 as shown in FIG. 6, however in other embodiments circulating pump 190 may be external to device 110. Regardless of whether a circulating pump is included, the closed loop (e.g., FIGS. 6-7) or static closed (e.g., FIG. 5) system provides fluid-based heating or cooling of samples without samples 140 contacting the fluid heating/ cooling medium within pillows 130, thereby substantially avoiding potential for contamination of sample 140.

The functions of console unit 110, including heating, cooling, motion, monitoring, and others may be powered by a conventional electric power input 219, shown in FIGS. 9-11. Additionally, a battery backup 221 may be provided in the event of power loss, which may be, e.g., a result of moving the portable console unit 110 to a location without a power source.

In some embodiments, such as shown in FIG. 11, reservoirs 202, 204 may be provided within console unit 110 for cooling fluid and heating fluid respectively. Fluid cooling reservoir 202 and its associated pump (not shown) cools the fluid used in pillows 130 to exchange heat with sample 140, and pumps it along a valved flow line into pillow 130. Fluid cooling reservoir 202 also receives fluid from pillows 130 for cooling. Similarly, fluid heating reservoir 204 and its associated pump (not shown) warms the fluid used in pillows 130 to exchange heat with sample 140, and pumps it along a valved flow line into pillow 130 to increase the temperature of pillow 130. Fluid heating reservoir 204 also receives fluid from pillows 130 to be warmed.

Figure 14:
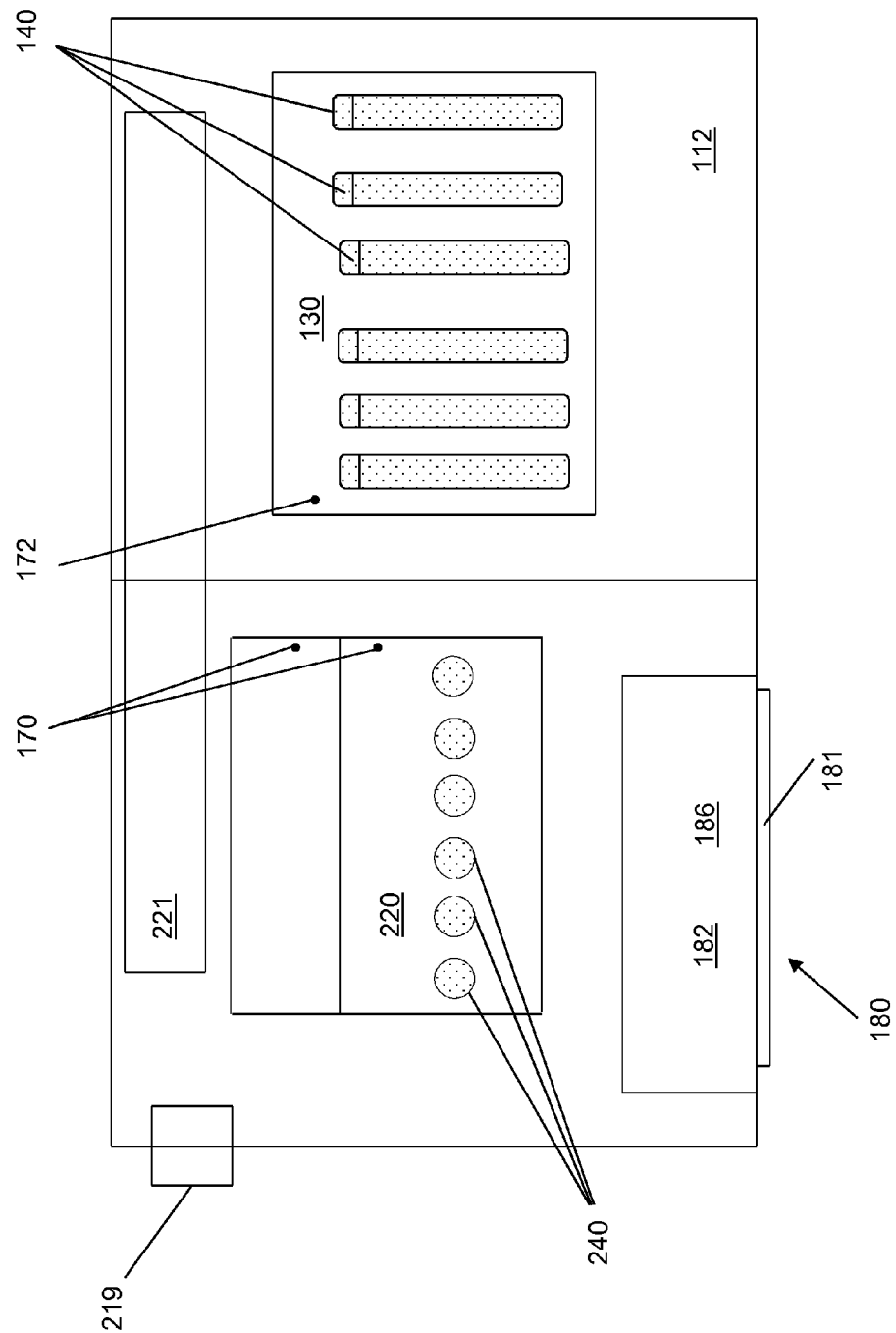
FIG. 14 shows a top view of a console unit including an integrated frozen sample holding chamber, according to an embodiment of the invention.
Figure 15:
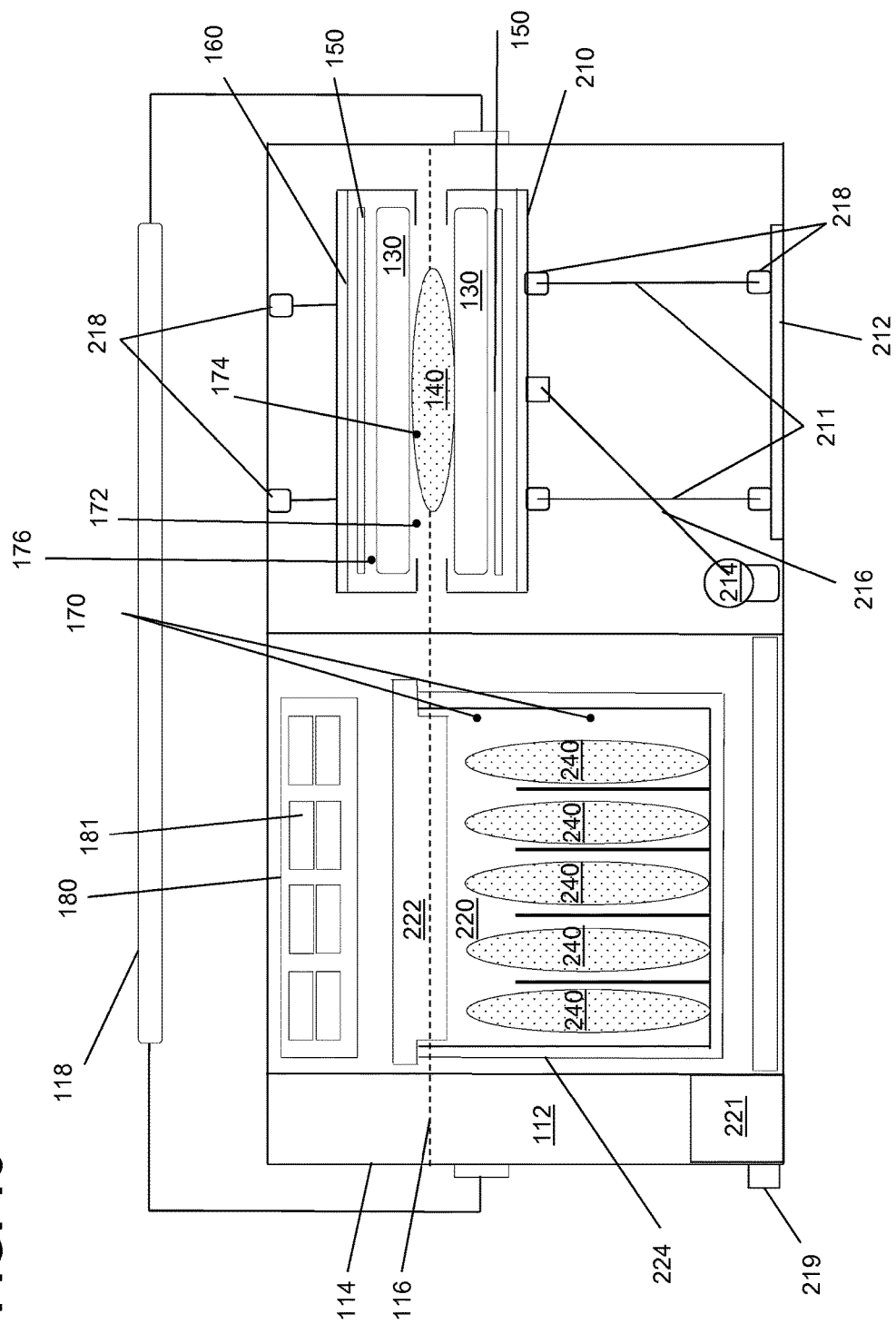
FIG. 15 shows a cross sectional view of a console unit including an integrated frozen sample holding chamber, according to an embodiment of the invention.
Figure 16:
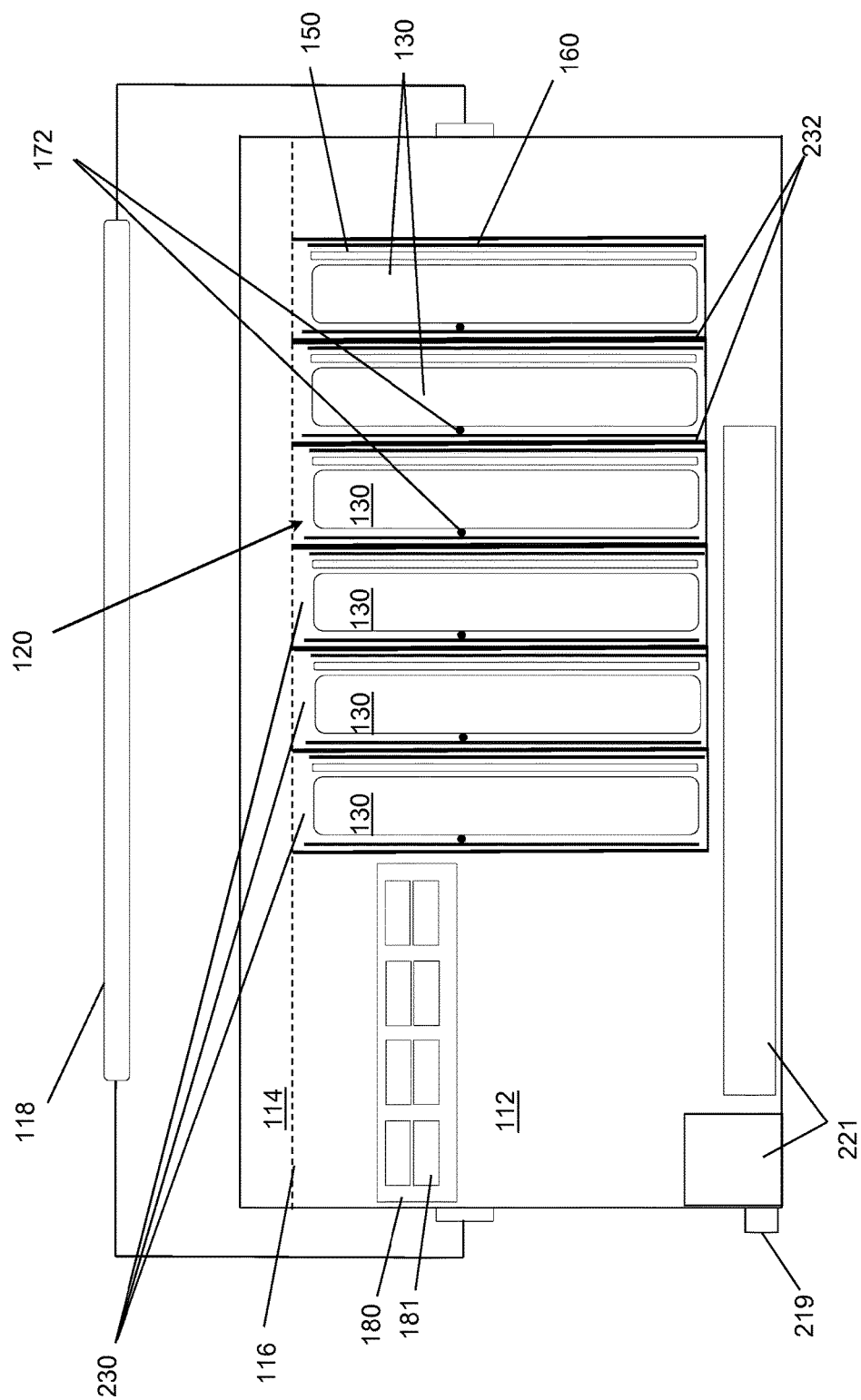
FIG. 16 shows a cross sectional view of a console unit including heating chambers for removable pillows, according to an embodiment of the invention.

Turning next to FIGS. 14-15, these figures illustrate top and cross sectional views, respectively, of a console unit 110 that includes a holding chamber 220 for storing still-frozen samples 240. Insulated holding chamber 220 is disposed within console 110, and may include an insulated lid 222 and, within holding chamber 220, a plurality of insulated slots or spaces 224 for storing frozen samples 240 for future thawing using pillows 130.

In FIG. 16, another embodiment is shown including a plurality of heating or cooling chambers 230 for warming or cooling removable pillows 130. In such an embodiment, pillows 130 may be heated or cooled in chamber 120, then removed for heating/cooling of a subject outside of console 110. Each chamber 230 is separated from each other chamber 230 by an insulating partition or divider 232. Within each warming or cooling chamber 230 is a thermal device 150 and a pillow 130 disposed therein. Pillow 130 is heated or cooled by thermal device 150 within chamber 230, and may then be removed from console unit 110 for use to heat or cool another sample or object. Such an embodiment may be used for the heating of pillows 130 for use as a topical heating pad device.

In various embodiments, system control center 180 may include a computing device 182 (FIGS. 11, 12, 14) including hardware with instructions stored thereon for carrying out a variety of operational and monitoring functions. Computing device 182 may be internal relative to console unit 110 (FIGS. 11, 12, and 14), or may be an external device (schematic shown in FIG. 19). In some embodiments (FIG. 13), system control center 180 may include both internal and external components.

Figure 12:
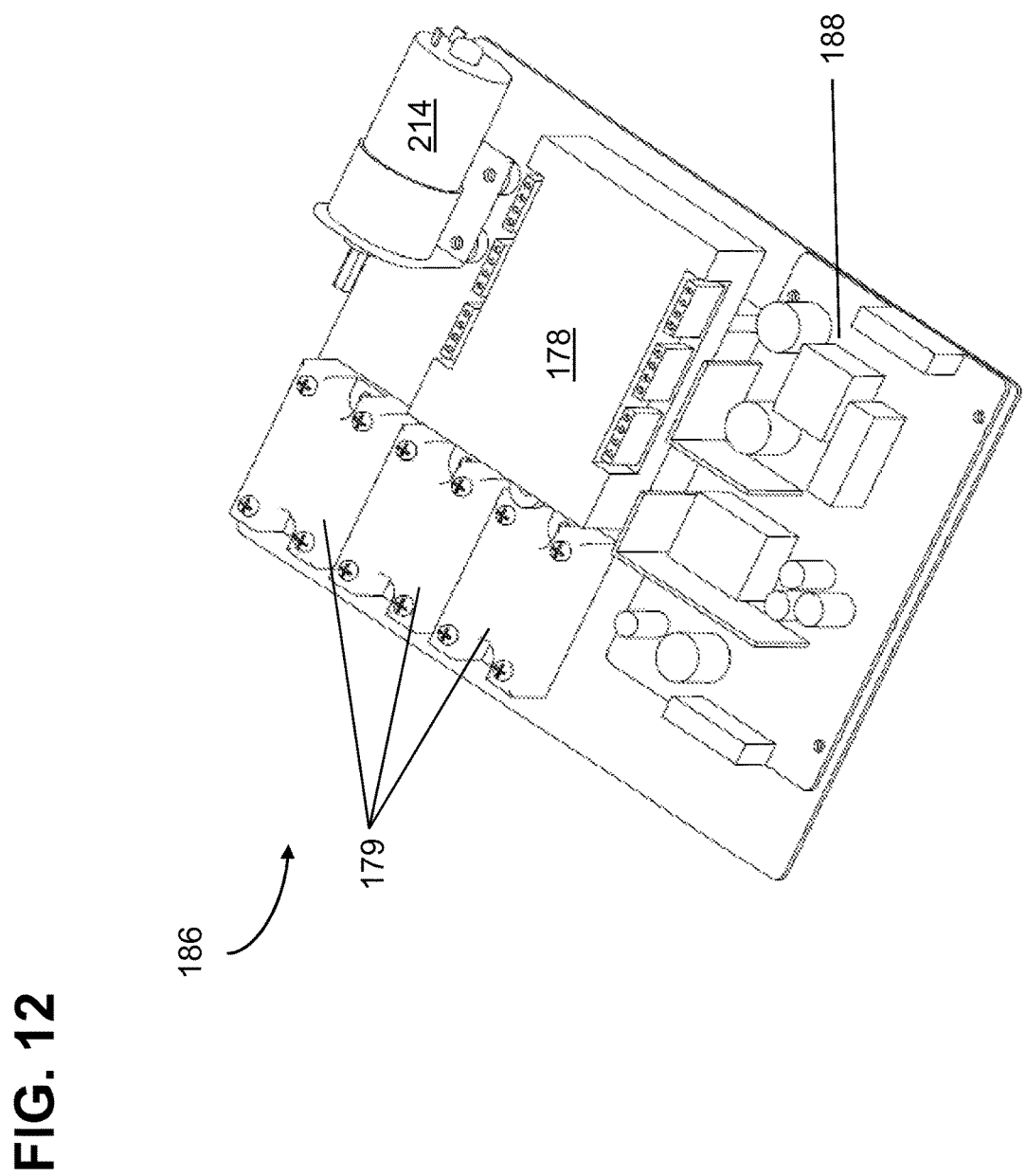
FIG. 12 shows a perspective view of electronic control aspects of an embodiment of the invention.

FIG. 12 illustrates a number of components of system control center 180 which may be internal relative to console unit 110. These components may include, e.g., power supply 188, microprocessor/control board 178, and a series of electronic relays and boards 179. These components may make up, be part of, and/or be contained within an electronic control board assembly 186 within the system control center 180 (FIG. 13), for controlling and/or monitoring various aspects of the system including the temperature control devices, motor, motion, operation, temperature sensors, and timers, among others. These internal components forming system control center 180 may further contain circuitry which provides for integrated control of system operation, such that console unit 110 can be used as a standalone unit (e.g., FIG. 12) or can be configured to interface with an external computing device 182 (e.g., FIG. 13) to provide or augment operational control.

Figure 19:
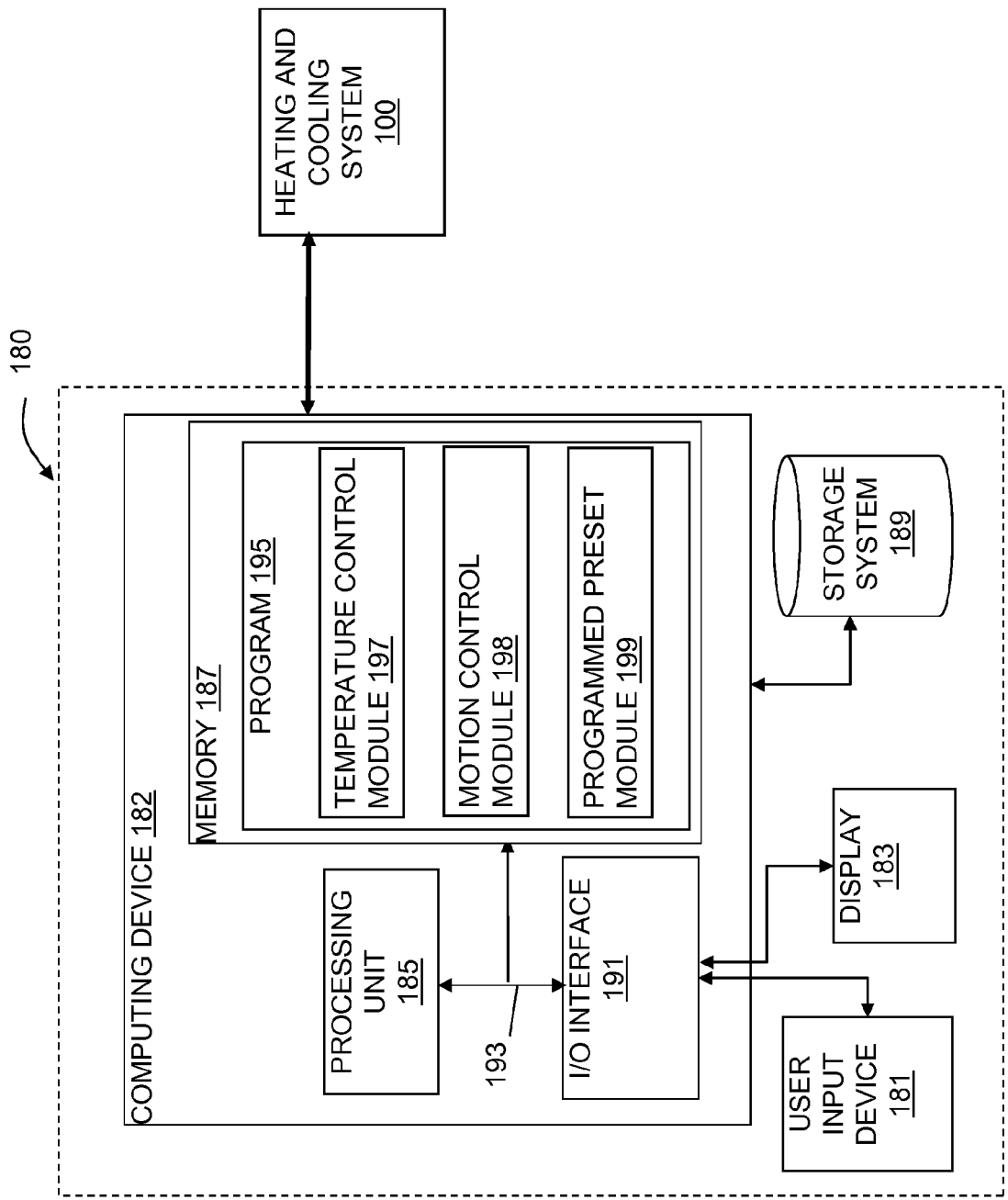
FIG. 19 shows a schematic drawing of aspects of the system control center according to an embodiment of the invention.

Computing device 182, shown in context in FIG. 13 and in schematic detail in FIG. 19, may include a processing unit 185 (e.g., one or more processors), a memory 187, a storage system 189, an input/output (I/O) interface component 191 (e.g., one or more I/O interfaces and/or devices) and a communications pathway 193. Computing device 182 may be in communication with internal components (e.g., 178, 179) of console unit 110 or may provide the functions thereof.

In general, processing unit 185 executes program code, such as temperature control program 195, which is at least partially fixed in memory 187. Memory 187 can include local memory, employed during actual execution of the program code, bulk storage (storage 189), and/or cache memories (not shown) which provide temporary storage of at least some program code in order to reduce the number of times code must be retrieved from bulk storage 189 during execution. As such, memory 187 may comprise any known type of data storage media, including magnetic media, optical media, random access memory (RAM), read-only memory (ROM), a data cache, a data object, etc. Moreover, memory 187 may reside at a single physical location, comprising one or more types of data storage, or be distributed across a plurality of physical systems in various forms.

While executing program code, processing component 185 can process data, which can result in reading and/or writing transformed data from/to memory 187 and/or I/O component 191 for further processing. Pathway 193 provides a direct or indirect communications link between each of the components in computing device 182. I/O interface component 191 can comprise one or more human I/O devices, which enable a human user 120 to interact with computing device 182. I/O interface component 191 may include a control panel or user input device 181 in the form of, e.g., a keypad, buttons, dials, or other user input mechanisms, and a display 183. As components of computing device 182, user input device 181 and display 183 may either be integrated with console unit 110 (FIGS. 14, 16) or on an external device (FIG. 13) as will be appreciated by one of skill in the art.

To this extent, temperature control program 195 can manage a set of interfaces (e.g., graphical user interface(s), application program interface, and/or the like) that enable human and/or system users to interact with temperature control program 195. As used herein, it is understood that "program code" means any collection of instructions, in any language, code or notation, that cause a computing device having an information processing capability to perform a particular action either directly or after any combination of the following: (a) conversion to another language, code or notation; (b) reproduction in a different material form; and/or (c) decompression. To this extent, temperature control program 195 can be embodied as any combination of system software and/or application software.

Temperature control program 195 can be implemented using a set of modules 197-199. In this case, a module 197-199 can enable computing device 182 to perform a set of tasks used by temperature control program 195, and can be separately developed and/or implemented apart from other portions of temperature control program 195. As used herein, the term "component" means any configuration of hardware, with or without software, which implements the functionality described in conjunction therewith using any solution, while the term "module" means program code that enables a computing device 182 to implement the actions described in conjunction therewith using any solution. When fixed in a memory 187 of a computing device 182 that includes a processing component 185, a module is a substantial portion of a component that implements the actions. Regardless, it is understood that two or more components, modules, and/or systems may share some/all of their respective hardware and/or software. Further, it is understood that some of the functionality discussed herein may not be implemented or additional functionality may be included as part of computing device 182.

Monitoring probes may be disposed in a variety of locations within insulated chamber 120, and may transmit data collected on various system parameters to system control center 180 for monitoring. These parameters may include, e.g., temperatures within or on any of a plurality of points on any thermal device 150, sample 140, or pillow 130, a flow rate of fluid through a closed loop circuit between a circulating pump 190 and a pillow 130, and any other attributes of the system.

In various embodiments, the monitoring probes may more specifically include temperature measurement devices (e.g., thermocouples) 172 disposed on pillows 130, temperature measurement devices (e.g., thermocouples) 174 disposed on samples 140, and/or temperature measurement devices (e.g., thermocouples) 176 disposed on thermal devices 150. In some embodiments (FIGS. 14-15), temperature measurement devices 170 may further be disposed within the second holding chamber 220. Temperature measurement devices 170, 172, 174, 176 may transmit a signal via, e.g., a wired or wireless connection to system control center 180 representing a temperature of the pillow 130, sample 140, or thermal device 150 with which it is in contact. Temperature measurement devices 174 may be affixed to an exterior of one or more samples 140 in any known manner including, e.g., adhesives, bands or straps, and merely being placed into contact with sample 140 while enclosed within temperature control chamber 120. Temperature measurement devices 172 (and similarly 170, 174, 176) may further be part of an assembly, illustrated in FIGS. 17 (collapsed) and 18 (extended) which may be coupled to console unit 110 via a connection port 111 (FIG. 3). With reference to FIG. 13, any of temperature measurement devices 170, 172, 174, 176 or other monitoring probes may be wired, e.g. via connection port 111 (FIG. 3), such that they are in signal communication with control system 180, including computing device 182. Via this signal communication pathway, monitoring probes including temperature measurement devices 170, 172, 174, 176 can provide feedback to computing device 182 to facilitate execution of a pre-determined (either preset or user-specified) heating or cooling cycle. It is noted that although a wired communication link is shown, any combination of various types of wired and/or wireless links, and any combination of various types of transmission techniques and protocols may be used.

As discussed herein, temperature control program 195 enables computing device 182 to implement control of the temperature, rate of temperature change, motion, and other parameters of a sample 140 held within the device. To this extent, temperature control program 195 is shown including a temperature control module 197 for receiving temperature feedback data and sending heating/cooling commands to the device, a motion control module 198 for receiving motion data and sending commands to start, stop, speed up, or slow movement of the motion table, and a programmed preset module 199, for storing and executing preset warming/cooling programs. These modules are merely exemplary; others may also be employed to carry out additional functions.

User input device 181 may be used to enter any of a variety of operational parameters including but not limited to: the desired temperature to which a sample is to be heated, a desired rate of heating or cooling (e.g., in ° C. per minute), a pre-programmed or preset rate curve for heating or cooling which may vary throughout the course of a heating or cooling cycle, and a specified action to be taken upon determination via monitoring probes that the desired temperature has been achieved. In various embodiments, the specified action may be, e.g., opening console lid 114, moving a sample 140 tray/fixture away from pillows 130, sounding an alarm, displaying a message, and/or adjusting heating or cooling conditions within chamber 120.

Regardless of the internal (FIGS. 11, 12, 14) or external (FIG. 13) location of various elements of system control center 180, system control center 180 and/or electronic control board assembly 186 may display data received from temperature measurement devices 170, 172, 174, 176 to a user in real time, e.g., via a screen display 183, which may be integrated with console unit 110 (FIG. 1) or an external device (FIG. 19). Such data may also be used by system control center 180 in a feedback loop to actively adjust the power or output of thermal devices 150 or other elements, therefore adjusting the temperature of the device, and/or adjusting fluid movement (e.g., through circulation pump 190) within pillows 130 throughout a heating or cooling cycle.

Further, system control center 180 may be in electronic signal communication with any of a number of operational elements of console unit 110, such as thermal devices 150, via a communication link similar to that described relative to the temperature measurement devices such that system control center 180 controls operation of each of the elements. System control center 180 may use data from temperature sensors 172, 174, 176 to automatically carry out any of the foregoing tasks, and/or a digital or analog timer for tracking pre-warming and/or heating cycle time. In various embodiments, each thermal device 150, cooling unit 196, circulating pump 190, and other elements may be independently and manually or automatically controlled, monitored, and adjusted. Each element may also be independently programmable to accommodate different heating or cooling parameters of a sample at the same time.

System control center 180 may additionally store data representing measurements taken by temperature sensors 170, 172, 174, 176 and other monitoring probes. System control center 180 may be configured to store a log of operational conditions including e.g., elapsed time, sample, pillow, and heater temperatures, motion, and other conditions as reported by monitoring probes. These data may be stored in, e.g., storage system 189 (FIG. 19).

To use the device, a pre-set or user-specified temperature may be entered via the control panel 181, and thermal devices 150 warm pillows 130 with lid 114 closed. The preset or user-specified temperature may be optimized for heating rate/time. Once pillows 130 reach the desired set temperature, lid 114 may be opened at latch 184 (FIG. 14), exposing the pillows 130. A sample(s) 140 may be placed on the thermal pillows 130, the lid 114 is closed, and the samples 140 are thawed, either for a pre-determined period of time, or until monitoring probes 170 indicate that a specific temperature has been attained. The unique compliant design of the thermal pillow 130 allows for highly effective surface contact and heat transfer between the frozen sample 140 and the pillow 130 on all sides throughout the thawing process regardless of the container shape. Alternatively, samples 140 can be placed into the system at anytime prior to, during or following temperature activation of the system to provide for alternate warming or cooling profiles of said sample.

The device described above has been tested and compared to a standard 37° C. warm water bath protocol using a commonly employed human prostate cell model (PC-3) in standard 2.0 ml cryovials. Heating and cooling system 100, with pillows 130 set to 40° C., generated thawing rates (approaching 60° C./minute) similar to that of the standard water bath protocol. Specifically, a cryopreserved 1.0 ml sample was thawed from −196° C. to 4° C. in approximately 3 minutes, which is comparable to a water bath, while providing for a clean, controlled and documentable process which is not possible with a water bath thaw protocol. This set of time, temperature, and sample volume parameters is for illustrative purposes only, as time and temperatures will vary based on sample and system starting temperature, pillow temperature, sample volume, container type and sample type among other factors.

Further, through control processes, the warming rate profile could be modulated, including heating rates from 40° C./minute to 100° C./minute. The ability to control the warming rate allows a user to customize the rate (time) of the heating or cooling process based on individual parameters, optimizing the conditions for the user's samples. Assessment of cell viability following thawing revealed similar survival results using heating and cooling system 100 as compared to a warm water bath. This pattern was observed across a variety of carrier media and cryoprotective agent concentrations. For example, PC-3 cells cryopreserved in media+10% dimethyl sulfoxide (DMSO) under a controlled rate freezing protocol and thawed using heating and cooling system 100 or a water bath yielded a 24 hour post thaw cell viability of ~81% (±5%) and 89% (±6%), respectively.

In parallel sets of experiments using the carrier solution Viaspan+15% DMSO, viabilities of 68% (±4%) and 71% (±2%), respectively, were obtained. Follow up assessment of the populations over a 3 day post-thaw recovery demonstrated that the surviving cells were able to divide in culture. Similar outcomes have been achieved using 25 ml cell therapy bags, 250 and 500 ml IV and blood bags, straws and cell culture plates.

As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). The suffix "(s)" as used herein is intended to include both the singular and the plural of the term that it modifies, thereby including one or more of that term (e.g., the metal(s) includes one or more metals). Ranges disclosed herein are inclusive and independently combinable (e.g., ranges of "up to about 25 mm, or, more specifically, about 5 mm to about 20 mm," is inclusive of the endpoints and all intermediate values of the ranges of "about 5 mm to about 25 mm," etc.).

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A system for controlling a temperature of a sample, comprising:
   an insulated chamber;
   at least one compliant vessel disposed within the chamber;
   at least one thermal device configured to attain a predefined temperature, disposed within the chamber and in physical contact with a wall of the at least one compliant vessel; and
   a fluid disposed within the at least one compliant vessel and contained in a closed system within the chamber such that the chamber is dry,
   wherein an outer surface of the at least one compliant vessel is in contact with and substantially conforms to a container containing the sample.

2. The system of claim 1, wherein the fluid in the compliant vessel is one of: water, an alcohol, an oil, ethylene glycol, an aqueous solution, an aqueous suspension, or a slurry.

3. The system of claim 2, wherein the fluid further comprises solid particles suspended therein.

4. The system of claim 1, wherein the compliant vessel comprises a sealed sac made of one of: a flexible plastic, a metallic material, a metallized plastic, a metal foil, a thermoplastic, or a waterproof fabric or leather, and the fluid is entirely contained within the compliant vessel.

5. The system of claim 1, wherein the closed system further includes a circulating pump fluidly connected to the compliant vessel by an inbound flow line and an outbound flow line, the circulating pump being configured to circulate fluid within each of the at least one compliant vessel, wherein the circulating pump and the compliant vessel,
   wherein the fluid is entirely contained within the compliant vessel, the circulating pump, and the inbound and outbound flow lines.

6. The system of claim 1, further comprising a motion table on which the compliant vessel and the sample are disposed, wherein the motion table is configured to move in an oscillating, rocking, vibrating, or shaking motion.

7. The system of claim 6, further comprising a flywheel coupled to a drive shaft, the drive shaft being further coupled to the motion table to generate an oscillating or a rocking motion.

8. The system of claim 1, wherein the at least one compliant vessel disposed within the chamber further comprises a first compliant vessel and a second compliant vessel, and wherein each of the first and the second compliant vessels is in contact with a thermal device of the at least one thermal device.

9. The system of claim 8, wherein the insulated chamber further comprises a base and a lid.

10. The system of claim 9, wherein the first compliant vessel is disposed within the base, and the second compliant vessel fluid filled is affixed to an interior of the chamber lid, such that when the lid is closed on the base, the container containing the sample is disposed between and is in contact with both of the first and the second compliant vessels.

11. The system of claim 10, further comprising a baseplate spring-mounted to the base, wherein the baseplate is configured to adjustably provide a pressure on the first compliant vessel against the second compliant vessel.

12. The system of claim 1, further comprising at least one temperature sensor disposed on one or more of: the container containing the sample container, the thermal device, or the compliant vessel.

13. The system of claim 12, further comprising:
a plurality of temperature sensors disposed on each of a plurality of compliant vessels; and
a plurality of temperature sensors disposed on each of a plurality of sample containers.

14. The system of claim 12, further comprising a system control center in signal communication with the at least one temperature sensor, the system control center including a computing device configured to:
receive user input via a user input device, the user input including at least one of:
a pre-defined temperature to which the sample is to be heated,
a desired rate of heating or cooling, or
a specified action to be taken upon determination that the pre-defined temperature has been achieved, wherein the specified action is one of: opening the insulated chamber, moving a sample container away from the at least one compliant vessel, sounding an alarm, displaying a message on a display unit, or adjusting an output of the thermal device within the insulated chamber;
execute, via controlling output of the thermal device, a temperature adjustment of the sample container in accordance with the user input; and
receive temperature feedback data from the at least one temperature sensor, wherein the executing is based at least in part on the temperature feedback data.

15. The system of claim 14, wherein the computing device is further configured to store the temperature feedback data and create a log documenting conditions during a temperature adjustment cycle.

16. The system of claim 14, wherein the computing device is further configured to receive and store time and motion table data.

17. The system of claim 1, further comprising a second insulated chamber for holding and maintaining a temperature of one or more samples.

18. The system of claim 17, further comprising at least one temperature sensor disposed within the second insulated chamber, for monitoring a temperature within the second insulated chamber.

19. The system of claim 1, wherein the at least one thermal device includes a heating device selected from a group consisting of: a thermoelectric heating pad, a Peltier heater, a cartridge heater, a resistance wire, and a heat pump.

20. The system of claim 1, wherein the at least one thermal device includes a cooling device selected from a group consisting of: a Peltier device and a refrigeration pump.

* * * * *